United States Patent
Kaneko et al.

(10) Patent No.: US 8,428,218 B2
(45) Date of Patent: Apr. 23, 2013

(54) DYNAMIC TUMOR RADIATION TREATMENT APPARATUS AND PROGRAM

(75) Inventors: Junichi Kaneko, Sapporo (JP); Fumiyuki Fujita, Sapporo (JP); Hiroki Shirato, Sapporo (JP); Eiji Takada, Toyama (JP)

(73) Assignees: National University Corporation Hokkaido University, Hokkaido (JP); Institute of National Colleges of Technology, Japan, Tokyo (JP)

( * ) Notice: Subject to any disclaimer, the term of this patent is extended or adjusted under 35 U.S.C. 154(b) by 579 days.

(21) Appl. No.: 12/449,682

(22) PCT Filed: Feb. 21, 2008

(86) PCT No.: PCT/JP2008/052944
§ 371 (c)(1),
(2), (4) Date: Dec. 22, 2009

(87) PCT Pub. No.: WO2008/102843
PCT Pub. Date: Aug. 28, 2008

(65) Prior Publication Data
US 2010/0142677 A1    Jun. 10, 2010

(30) Foreign Application Priority Data
Feb. 21, 2007 (JP) .................................. 2007-041373

(51) Int. Cl.
*A61N 5/10* (2006.01)
*H05G 1/00* (2006.01)
*G01T 1/16* (2006.01)

(52) U.S. Cl.
USPC ............... 378/65; 378/95; 250/362; 250/587

(58) Field of Classification Search ............. 378/62, 378/63, 65, 95, 120, 205; 250/580–587, 250/362, 363.01, 363.02, 363.03, 363.04, 250/370.09, 269.3
See application file for complete search history.

(56) References Cited

U.S. PATENT DOCUMENTS

| | | | |
|---|---|---|---|
| 7,221,733 B1* | 5/2007 | Takai et al. ................ | 378/65 |
| 2003/0108147 A1* | 6/2003 | Kojima et al. .............. | 378/19 |
| 2004/0138557 A1 | 7/2004 | Le et al. | |

FOREIGN PATENT DOCUMENTS

| | | |
|---|---|---|
| JP | S64-027569 | 1/1989 |
| JP | H02-099075 | 4/1990 |

(Continued)

OTHER PUBLICATIONS

"Detection of Lung Tumor . . . " by Shinichi Shimizu et al., in International Journal of Radiation: Oncology Biology Physics, vol. 51, No. 2, Jan. 1, 2001, pp. 304-310.

*Primary Examiner* — Anastasia Midkiff
(74) *Attorney, Agent, or Firm* — DLA Piper LLP (US)

(57) ABSTRACT

A dynamic tumor radiation treatment program for causing a computer to function. The program includes detecting an annihilation gamma ray with a gamma ray detector, storing the threshold of counting rate in a displacement threshold memory, computing the counting rate according to the detection signal of an annihilation gamma ray with a gamma ray counting rate computer, comparing the counting rate of annihilation gamma rays acquired from the gamma ray counting rate computer with the threshold of the counting rate acquired from the displacement threshold storage memory by means of a threshold comparator, judging whether or not the tumor is displaced out of the radiation irradiation spot by means of a tumor position judging unit, and making a control to stop radiation irradiation or outputting a stop command signal by means of an irradiation controller.

9 Claims, 13 Drawing Sheets

FOREIGN PATENT DOCUMENTS

| | | |
|---|---|---|
| JP | 10-34423 | 12/1998 |
| JP | 2004-533273 | 11/2004 |
| JP | 2005-514969 | 5/2005 |
| WO | WO 2007/017847 A | 2/2007 |

* cited by examiner

DYNAMIC TUMOR RADIATION TREATMENT APPARATUS AND PROGRAM

TECHNICAL FIELD

The present invention relates to a radiation treatment apparatus for treating a tumor by irradiating with radiation, more particularly to a dynamic tumor radiation treatment apparatus and program suitable for treating a tumor, such as human lung cancer and gastric cancer, which is dynamically displaced due to respiration and movement of an organ.

BACKGROUND ART

A conventional radiation treatment apparatus, in which a malignant tumor such as cancer is irradiated with radiation to annihilate the malignant tumor, is proposed. Some technologies for irradiating a tumor which has been displaced by patient's respiration (e.g. human lung cancer) with radiation by tracing the movement thereof are also introduced.

For example, Japanese Patent No. 3053389 discloses a moving body tracing/irradiating apparatus which traces the position of a dynamically displaced tumor by implanting a marker such as gold that a fluoroscope can detect near an in vivo tumor and performing image analysis by the variable density regulating cross-correlation method based on the images obtained by the fluoroscope and calculating the position of the marker (Patent Document 1). In this method, a dynamically displaced tumor in vivo is selectively irradiated with radiation to reduce the unnecessary radiation exposure to normal tissues.

Patent Document 1

Japanese Patent No. 3053389

DISCLOSURE OF THE INVENTION

Problem to be Solved

However, according to the invention described in the Patent Document 1, the patient requires a marker such as gold implanted in vivo, thereby causing the patient pain and heavy burden. A marker is implanted in vivo near a tumor to prevent diffusion and metastasis of cancer cells from tumor damage due to direct implantation of the marker, but implanting operation can be difficult and imperfect. Even if the marker is successfully implanted, the marker could be put in a wrong position thereafter, leading to limited practical use.

In addition, detection of a tumor site according to the Patent Document 1 requires many steps such as digitizing images obtained by a fluoroscope, conducting variable density regulating, analyzing images of the template of a tumor marker imaged beforehand by the variable density regulating cross-correlation method and obtaining a coordinate of the position of the tumor according to the analysis results. Subsequently, this process poses a major problem of radiation exposure due to continuous irradiation of strong X-rays on the patient. Heavy processing loads for imaging and calculating the position coordinate can fail to trace quick movement of the tumor, and operation costs become higher due to preparation of a computer with high processing capability.

To solve the aforementioned problems, the present invention provides a tumor radiation treatment apparatus and program which detects the position of a tumor with high accuracy without imposing a burden on the patient, continuously detects a tumor with high detection efficiency and effectively irradiates only a malignant tumor with radiation to reduce the radiation exposure dose.

Means for Solving the Problem

A dynamic tumor radiation treatment apparatus according to the present invention comprises gamma ray detecting means for detecting an annihilation gamma ray emitted from a radiopharmaceutical that accumulates in a tumor by dosing in vivo, displacement threshold storage means for storing the threshold of counting rate according to a relationship between said counting rate of the annihilation gamma ray and the displacement of a radiation source, gamma ray counting rate computing means for computing the counting rate according to the detection signal of an annihilation gamma ray detected by said gamma ray detecting means, threshold comparing means for comparing the counting rate of annihilation gamma rays acquired from said gamma ray counting rate computing means with the threshold of the counting rate acquired from said displacement threshold storage means, tumor position judging means for judging whether or not the tumor is displaced out of the radiation irradiation spot according to the results by said threshold comparing means and irradiation control means for making a control to stop radiation irradiation by the radiation irradiation means when said tumor position judging means judges that the tumor is displaced out of the radiation irradiation spot or for outputting a stop command signal.

In this invention, it is desirable that said gamma ray detecting means detect an annihilation gamma ray by a pair of gamma ray detectors oppositely disposed with a tumor in between and said gamma ray counting rate computing means compute a counting rate by simultaneously counting annihilation gamma rays.

A dynamic tumor radiation treatment apparatus according to the present invention comprises gamma ray detecting means for detecting an annihilation gamma ray emitted from a radiopharmaceutical that accumulates in a tumor by dosing in vivo by setting a plurality of measuring regions at a tumor boundary part or a boundary part of a stationary displaced tumor, boundary threshold storage means for storing the threshold of counting rate according to a relationship between said counting rate of the annihilation gamma ray and the displacement of a radiation source, gamma ray counting rate computing means for computing the counting rate according to the detection signal of an annihilation gamma ray detected by said gamma ray detecting means, threshold comparing means for comparing the counting rate of annihilation gamma rays acquired from said gamma ray counting rate computing means with the threshold of the counting rate acquired from said displacement threshold storage means, tumor position judging means for judging whether or not the tumor is displaced out of the radiation irradiation spot according to the results by said threshold comparing means and irradiation control means for making a control to stop radiation irradiation by the radiation irradiation means when said tumor position judging means judges that the tumor is displaced out of the radiation irradiation spot or for outputting a stop command signal.

Herein, it is desirable that said gamma ray detecting means compute counting rate of an annihilation gamma ray with a pair of gamma ray detectors oppositely disposed in each measuring region so that said gamma ray counting rate computing means simultaneously counts annihilation gamma rays detected by the pair of gamma ray detectors.

Also, in this invention, the threshold comparing means preferably acquires the threshold at a point of time according to counting rate of an annihilation gamma ray which declines as time elapses.

In this invention, said gamma ray detecting means preferably calculates counting rate by oppositely disposing another pair of gamma ray detectors in crossing direction to said a pair of gamma ray detectors oppositely disposed, so that said gamma ray counting rate computing means simultaneously counts annihilation gamma rays.

Furthermore, the present invention preferably comprises time difference position specifying means for specifying the position of a radiation source in length direction between a pair of gamma ray detectors by calculating a difference in arrival time of an annihilation gamma ray which arrives at the pair of gamma ray detectors.

A dynamic tumor radiation treatment program and a computer functioning by the program according to the present invention, wherein the computer comprises: gamma ray detecting means for detecting an annihilation gamma ray emitted from a radiopharmaceutical that accumulates in a tumor by dosing in vivo; displacement threshold storage means for storing the threshold of counting rate according to a relationship between said counting rate of the annihilation gamma ray and the displacement of a radiation source; gamma ray counting rate computing means for computing the counting rate according to the detection signal of an annihilation gamma ray detected by said gamma ray detecting means; threshold comparing means for comparing the counting rate of annihilation gamma rays acquired from said gamma ray counting rate computing means with the threshold of the counting rate acquired from said displacement threshold storage means; tumor position judging means for judging whether or not the tumor is displaced out of the radiation irradiation spot according to the results by said threshold comparing means; and irradiation control means for making a control to stop radiation irradiation by the radiation irradiation means when said tumor position judging means judges that the tumor is displaced out of the radiation irradiation spot or for outputting a stop command signal.

A dynamic tumor radiation treatment program and a computer functioning by the program according to the present invention, wherein the computer comprises; gamma ray detecting means for detecting an annihilation gamma ray emitted from a radiopharmaceutical that accumulates in a tumor by dosing in vivo, by setting a plurality of measuring regions at a tumor boundary part or a boundary part of a stationary displaced tumor; boundary threshold storage means for storing the threshold of counting rate according to a relationship between said counting rate of the annihilation gamma ray and the displacement of a radiation source in a measuring region; gamma ray counting rate computing means for computing the counting rate according to the detection signal of an annihilation gamma ray detected by said gamma ray detecting means; threshold comparing means for comparing the counting rate of annihilation gamma rays acquired from said gamma ray counting rate computing means with the threshold of the counting rate acquired from said displacement threshold storage means; tumor position judging means for judging whether or not the tumor is displaced out of the radiation irradiation spot according to the results by said threshold comparing means; and irradiation control means for making a control to stop radiation irradiation by the radiation irradiation means when said tumor position judging means judges that the tumor is displaced out of the radiation irradiation spot or for outputting a stop command signal.

Advantageous Effect of the Invention

The present invention can improve detection accuracy by imposing no burden on the patient and directly detecting the position of a tumor, reduce radiation irradiation on non-tumor cells by tracing accurately the movement of the tumor and continuously detect a tumor with high detection efficiency and effectively irradiate only a malignant tumor with radiation to reduce the radiation exposure dose and side effects.

BEST MODE FOR CARRYING OUT THE INVENTION

As a basic principle, the present invention specifies the position of a tumor with high accuracy by dosing a patient with a radiopharmaceutical which accumulates in the tumor and using an annihilation gamma ray emitted from the radiopharmaceutical as a marker.

According to the present invention, a first embodiment of a dynamic tumor radiation treatment apparatus is described with reference to the drawings. FIG. 1 is a block diagram indicative of overall structure of this first embodiment.

As shown in FIG. 1, a dynamic tumor radiation treatment apparatus 1 in this first embodiment essentially comprises radiation irradiation means 10 for irradiating a tumor with therapeutic radiation, gamma ray detecting means 20 for detecting a gamma ray, storage means 30 for storing a radiation treatment program of this first embodiment and other relevant data and computing means 40 for controlling each constitutive means and performing each arithmetic operation.

Each of the constitutive means will be described in detail. The radiation irradiation means 10 irradiates a tumor 50 with therapeutic radiation. In this first embodiment, the radiation irradiation means 10 comprises a radiation irradiation spot to be targeted (not shown). The tumor 50 in the radiation irradiation spot is irradiated with radiation to annihilate the tumor 50.

The gamma ray detecting means 20 detects an annihilation gamma ray emitted from a radiopharmaceutical that accumulates in the tumor 50. In the first embodiment, the gamma ray detecting means 20 comprises a pair of gamma ray detectors 21,22 oppositely disposed with the tumor 50 in between. The gamma ray detectors 21,22 mainly comprises a scintillator which detects radiation (not shown), a photomultiplier which converts the radiation detected by the scintillator into electrical signal (not shown) and a collimator 23 which is disposed on a detection surface of the scintillator to allow only a gamma ray coming in perpendicular to the detection surface to pass.

The storage means 30 essentially comprises a hard disk, furthermore comprising a program storage section 31 which stores a radiation treatment program of this first embodiment and a displacement threshold storage section 32. The displacement threshold storage section 32 stores the threshold of counting rate according to a relationship between the counting rate of the annihilation gamma ray and the displacement of a radiation source 61. The threshold is defined to determine whether or not the tumor 50 as a radiation source 61 has come in the radiation irradiation spot. As described later, the counting rate of an annihilation gamma ray becomes higher as the tumor 50 comes in the measuring region and the counting rate becomes smaller as the tumor 50 is displaced out of the measuring region, based on which, the threshold is determined. Also, a radionuclide which emits annihilation gamma rays declines as time elapses. For example, F-fluorodeoxyglucose (FDG) as a radionuclide decreases by half in approx. 2 hours. Therefore, the threshold of an annihilation gamma ray is set in an adjustable manner as time elapses. The threshold may be stored as a table in accordance with time elapsed or calculated by a function expression of an elapsed time stored in a program and substituting an acquired elapsed time therein.

The computing means 40 essentially comprises central processing unit (CPU). By executing a radiation treatment program in the program storage section 31, the computing means 40 comprises a counting rate computing section 41, a time measuring section 42, a threshold comparing section 43, a tumor position judging section 44 and an irradiation control section 45 on a computer functioning by the program.

Each component of the computing means 40 will be described in more detail.

The counting rate computing section 41 calculates counting rate defined as the number of an annihilation gamma ray emitted per unit time by acquiring detection signal of annihilation gamma rays detected by the gamma ray detecting means 20. In this first embodiment, the counting rate computing section 41 comprises a simultaneous counting circuit for a gamma ray to calculate the counting rate by simultaneously counting detection signals outputted from a pair of detectors.

The time measuring section 42 measures the duration required for a nuclide in a radiopharmaceutical to decline as time elapses. Specifically, the time measuring section 42 measures the duration of the counting rate of an annihilation gamma ray to decline, on the basis of the time for the radiopharmaceutical to be dosed or the time for a threshold to be stored in the displacement threshold storage section 32.

The threshold comparing section 43 acquires counting rate of an annihilation gamma ray calculated by the counting rate computing section 41 and a threshold of the counting rate according to an elapsed time from the displacement threshold storage section 32 to make a comparison therebetween. Specifically, the threshold comparing section 43 acquires an elapsed time from the time measuring section 42 and a threshold according to the elapsed time from the displacement threshold storage section 32. When the threshold is determined by an expression in accordance with the elapsed time, the threshold comparing section 43 calculates the threshold in accordance with the elapsed time.

The tumor position judging section 44 judges whether or not the tumor 50 is displaced out of a radiation irradiation spot based on the results by the threshold comparing section 43. Specifically, when the counting rate of a detected annihilation gamma ray is lower than a threshold, a tumor 50 is out of the irradiation spot, and when the counting rate corresponds to a threshold or more, the tumor 50 is within the irradiation spot.

The irradiation control section 45 controls the operation of the radiation irradiation means 10. In this first embodiment, the irradiation control section 45 stops radiation irradiation by the radiation irradiation means 10 when the tumor position judging section 44 judges that the tumor 50 is displaced out of the irradiation spot. Also, output means such as display (not shown) and warning light may indicate a command to stop radiation. A user can manually stop irradiation by the radiation irradiation means 10 by confirming a stop command by the output.

Next, the operation of a dynamic tumor radiation treatment apparatus 1 executed by a dynamic tumor radiation treatment program in this first embodiment will be described with reference to FIG. 2. In this first embodiment, to start with radiotherapy, a radiopharmaceutical is dosed to a patient beforehand. Thereafter, a radiopharmaceutical dosed accumulates in the tumor 50 to emit annihilation gamma rays, which will be detected.

Firstly, the gamma ray detecting means 20 detects an annihilation gamma ray (step S1) to specify the stationary and dynamic positions of the tumor 50 and set a measuring region 51 (step S2). In this first embodiment, gamma ray detectors 21,22 oppositely disposed with the tumor 50 in between detects an annihilation gamma ray emitted from the radiopharmaceutical in vivo. Here, the gamma ray detectors 21,22 detect an annihilation gamma ray emitted between the gamma ray detectors 21,22 which come in perpendicular to a detection surface. Then, the counting rate computing section 41 acquires a detection signal from the gamma ray detectors 21,22, calculates counting rate of annihilation gamma rays by simultaneous counting and specifies the position of the tumor 50, based on a threshold obtained by a relationship between the counting rate and the position (distance) of a radiation source 61. The measuring region 51 of the gamma ray detecting means 20 is preferably set at a position where the dynamic tumor 50 is stationary.

Subsequently, a radiation irradiation spot of the radiation irradiation means 10 is set (step S3) at a position where the tumor 50 is stationary, by specifying the position and movement of the dynamic tumor, based on the measurement results of said gamma ray detecting means 20. Thereafter, the tumor 50 in the radiation irradiation spot is irradiated with radiation (step S4), thereby effectively annihilating the tumor irradiated with radiation.

Meanwhile, the gamma ray detecting means 20 detects an annihilation gamma ray emitted from a radiopharmaceutical that continuously accumulates in the tumor 50 by the gamma ray detectors 21,22 (step S5). Then, the counting rate computing section 41 receives a detection signal of annihilation gamma rays from the gamma ray detectors 21,22 to calculate the counting rate by simultaneous counting. The threshold comparing section 43 acquires counting rate from said counting rate computing section 41 and the threshold of the counting rate from displacement threshold storage section 32 to make a comparison therebetween (step S6).

Next, the tumor position judging section 44 judges whether or not the tumor 50 is displaced out of the radiation irradiation spot based on the results by the threshold comparing section 43 (step S7). Specifically, when the counting rate is the threshold or more, the tumor 50 is in the irradiation spot, and when the counting rate is lower than the threshold, the tumor 50 is displaced out of the radiation irradiation spot.

When the irradiation control section 45 judges that the tumor 50 is displaced out of the radiation irradiation spot (step S7:YES) based on the results of said tumor position judging section 44, radiation irradiation stop control is made (step S8). Meanwhile, when the tumor 50 is in the radiation irradiation spot (step S7: NO), the irradiation control section 45 will stop the operation and the process returns to the step S4 to continue radiation irradiation by the radiation irradiation means 10. Radiation irradiation and its stop may be conducted manually, instead of automatically. In the step S8, the irradiation control section 45 outputs a command to stop radiation irradiation by display, warning light, alarm, etc. to indication output means. A user can confirm this indication visually or acoustically and accordingly press the stop button for radiation irradiation.

The radiation irradiation means 10 judges whether or not radiation irradiation on the tumor 50 meets specified conditions according to radiation irradiation duration and radiation irradiation volume (step S9). If such conditions are not fulfilled, the process returns to the step S4 to continue radiation irradiation (step S9: NO), and if the conditions are met, radiation irradiation is stopped to end the therapy (step S9: YES).

The above described first embodiment has the following advantages:
1. Reduction in the burden on the patient in radiotherapy
2. More accurate radiation irradiation on a tumor 50 due to improvement in its detection accuracy by directly detecting the position of the tumor 50 and precise tracing of the movement of the tumor 50
3. Reduction in radiation exposure dose on the patient and side effects due to significant reduction in unnecessary radiation irradiation on non-tumor cells In the above-described gamma ray detecting means 20, said a pair of gamma ray detectors 21,22 oppositely disposed may be provided with another pair of gamma ray detectors 21,22 oppositely disposed in crossing direction, particularly in a direction perpendicular thereto. By this structure, displacement of a tumor in length direction can be detected, thereby accurately specifying the position of the tumor.

Using a plurality of pairs of gamma ray detectors 21,22, when the tumor position judging means judges that the tumor is displaced out of the irradiation spot based on any one of a plurality of pairs of gamma ray detectors 21,22, radiation irradiation is stopped or a command to stop is indicated.

The computing means 40 may comprise a time difference position specifying section 46 which calculates a difference in arrival time of an annihilation gamma ray which arrives at a pair of gamma ray detectors 21,22 and specifies the position of a radiation source in length direction between a pair of gamma ray detectors 21,22 from the difference in arrival time. Accordingly, without using a plurality of pairs of gamma ray detectors 21,22, the position of the tumor in length direction in a pair of gamma ray detectors 21,22 can be determined, thereby providing an effect of a simpler structure.

Next, a second embodiment of the present invention will be described. As for the structure in this second embodiment which is identical or equivalent to the structure of above-described first embodiment, the same signs are employed with no redundant descriptions.

In the above-described first embodiment, a measuring region 51 by the gamma ray detectors 21,22 is set at the center of a stationary tumor, but in this second embodiment, one or more measuring regions are set at boundary parts of a dynamically displaced tumor 52,53. The purpose of this second embodiment is to remove an error by annihilation gamma rays generated from a radiopharmaceutical which accumulates not only in the tumor but also in cells nearby.

A second embodiment of a dynamic tumor radiation treatment apparatus 1 according to the present invention will be described with reference to the drawings. FIG. 3 is a block diagram indicative of overall structure of this second embodiment.

As shown in FIG. 3, a dynamic tumor radiation treatment apparatus 1 in this second embodiment essentially comprises radiation irradiation means 10 for irradiating a tumor with therapeutic radiation, gamma ray detecting means 20 for detecting a gamma ray, storage means 30 for storing a radiation treatment program of this second embodiment and other relevant data and computing means 40 for controlling each constitutive means and performing each arithmetic operation.

Each of the constitutive means will be described in more detail.

In this second embodiment, the gamma ray detecting means 20 detects an annihilation gamma ray emitted from one or more measuring regions 51 set at boundary parts of a dynamically displaced tumor 52,53. In this second embodiment, the gamma ray detecting means 20 comprises a pair of gamma ray detectors 21,22 oppositely disposed with each measuring region 51 in between, and a detected annihilation gamma ray is outputted to counting rate computing section 41 as a detection signal. In this second embodiment, as shown in FIGS. 5(A) and (B), the measuring region 51 may be set at a tumor boundary part 52 or a boundary part of a stationary displaced tumor 53 according to dynamic displacement of the tumor.

The storage means 30 comprises a program storage section 31 which stores a radiation treatment program of this second embodiment and a boundary threshold storage section 33. The boundary threshold storage section 33 stores the threshold of counting rate set according to a relationship between the counting rate of an annihilation gamma ray and the displacement at a tumor boundary part 52 or a boundary part of a stationary displaced tumor 53. The threshold is defined to judge whether or not a tumor 50 as a radiation source 61 comes in a measuring region 51 set at boundary parts of a dynamically displaced tumor 52,53. As a radionuclide which emits annihilation gamma rays declines according to elapsed time as in the first embodiment, the threshold of the counting rate becomes smaller as time elapses. The threshold may be calculated at an appropriate interval by a function expression of an elapsed time.

By executing a radiation treatment program in the program storage section 31, the computing means 40 comprises counting rate computing section 41, time measuring section 42, threshold comparing section 43, tumor position judging section 44 and irradiation control section 45 on a computer functioning by the program.

Each component of the computing means 40 will be described in more detail. The counting rate computing section 41 and the time measuring section 42 calculate counting rate of an annihilation gamma ray as in the first embodiment according to detection signal acquired from the gamma ray detecting means 20.

The threshold comparing section 43 acquires counting rate of an annihilation gamma ray calculated by said counting rate computing section 41 and a threshold from boundary threshold storage section 33 according to an elapsed time by the time measuring section 42 to make a comparison therebetween.

The tumor position judging section 44 judges whether or not a tumor 50 is in the radiation irradiation spot based on the results by the threshold comparing section 43. This second embodiment provides two different settings of a measuring region 51 of gamma ray detectors 21,22 at a tumor boundary part 52 and a boundary part of a stationary displaced tumor 53. Specifically, as shown in FIG. 5(A), when a plurality of measuring regions are set at the tumor boundary part 52, the tumor position judging section 44 judges that the tumor is in the radiation irradiation spot if the counting rate of an annihilation gamma ray is over the threshold in all measuring regions 51. Conversely, if the counting rate of an annihilation gamma ray is under the threshold in any one of the measuring regions 51, the tumor is displaced out of the radiation irradiation spot.

Meanwhile, as shown in FIG. 5(B), when a plurality of measuring regions 51 are set at a boundary part of a stationary displaced tumor 53, the tumor position judging section 44 judges that the tumor is in the radiation irradiation spot when the counting rate of an annihilation gamma ray is under the threshold in all measuring regions 51. Conversely, the tumor position judging section 44 judges that the tumor is displaced out of the radiation irradiation spot when the counting rate of an annihilation gamma ray is over the threshold in any one of the measuring regions 51. This judgment can accurately find out the movement of a tumor that three-dimensionally is displaced and significantly reduce radiation irradiation on non-tumor cells.

Next, the operation of a dynamic tumor radiation treatment apparatus 1 executed by a dynamic tumor radiation treatment program in this second embodiment will be described with reference to FIG. 4. As in the first embodiment, a radiopharmaceutical is dosed to a patient in vivo prior to radiotherapy.

As in the above-described first embodiment, the gamma ray detecting means 20 detects an annihilation gamma ray (step S11), the position and dynamic displacement of a tumor as well and sets a measuring region 51 at a tumor boundary part 52 or a boundary part of a stationary displaced tumor 53 (step S12). Subsequently, a radiation irradiation spot of radiation irradiation means 10 is set (step S13) at a position where the tumor 50 becomes stationary, by specifying the position and movement of the dynamic tumor, based on the measurement results by said gamma ray detecting means 20. Thereafter, the radiation irradiation means 10 irradiates the tumor in the radiation irradiation spot with radiation to start radiotherapy (step S14).

Subsequently, the gamma ray detecting means 20 detects an annihilation gamma ray emitted from a radiopharmaceutical which continuously accumulates in a measuring region near the tumor by the gamma ray detectors 21,22 (step S15). Here, the gamma ray detectors 21,22 detect an annihilation gamma ray emitted between the gamma ray detectors 21,22 which come in perpendicular to a detection surface.

Next, the counting rate computing section 41 acquires a detection signal from said gamma ray detecting means 20 to calculate the counting rate of annihilation gamma rays. The threshold comparing section 43 acquires counting rate and the threshold of the counting rate from boundary threshold storage section 33 to make a comparison therebetween (step S16).

Next, the tumor position judging section 44 judges whether or not the tumor 50 is displaced out of the radiation irradiation spot based on the results by the threshold comparing section 43 (step S17). Specifically, when the measuring region 51 is set as shown in FIG. 5(A) and when the counting rate of annihilation gamma rays is the threshold or more in all measuring regions, the tumor 50 is in the radiation irradiation spot, and when the counting rate of annihilation gamma rays is lower than the threshold or less in any one of the measuring regions, the tumor 50 is displaced out of the radiation irradiation spot. Meanwhile, when a measuring region is set as shown in FIG. 5(B) and the counting rate of annihilation gamma rays is the threshold or less in all measuring regions, the tumor 50 is in the radiation irradiation spot. When the counting rate of annihilation gamma rays is the threshold or more in any one of the measuring regions, the tumor is displaced out of the radiation irradiation spot.

As in the first embodiment, when the tumor is in the radiation irradiation spot based on the results by said tumor position judging section 44, the irradiation control section 45 irradiates the tumor with radiation, and when the tumor is displaced out of the radiation irradiation spot, radiation irradiation stop control is made (step S17,S18).

Then, the irradiation control section 45 judges whether or not radiation irradiation on the tumor 50 meets specified conditions according to radiation irradiation duration and radiation irradiation volume (step S19). If such conditions are not fulfilled, the process returns to the step S14 to continue radiation irradiation (step S19: NO), and if the conditions are met, radiation irradiation is stopped to end the therapy (step S19: YES).

The above-described second embodiment provides an advantage of reducing unnecessary radiation irradiation on non-tumor cells of the patient and damage by a therapy due to side effects, etc. by preventing false judgment by annihilation gamma rays from a radiopharmaceutical which accumulates in cells near a tumor and specifying the position of the tumor with high accuracy, in addition to the advantages in the above first embodiment.

In this second embodiment, it is desirable that in order to specify the position of a tumor with higher accuracy, a plurality of measuring regions of gamma ray detectors 21,22 be set at a tumor boundary part 52 near the tumor. However, arrangement of many pairs of gamma ray detectors 21,22 will lead to more complicated configuration and higher costs. To solve this problem, the above-described time difference position specifying section 46 is preferably provided.

Example 1

Next, an experiment for determining the threshold of the counting rate of an annihilation gamma ray is described as Example 1.

FIG. 6 is a schematic view of a water phantom for a human lung used in the experiment. A cylindrical water phantom 60 with a diameter of 12 cm was prepared to simulate attenuation of a gamma ray by a human body and human lung part was simulated in styrene foam. For higher experimental accuracy, it is possible to set a mean density of a human lung ($\rho$) at 0.3 g/cm$^3$. The water phantom 60 is provided with a $^{22}$Na$\beta^+$ radiation source 61 at the center thereof as a substitute for F-fluorodeoxyglucose (FDG). The water phantom 60 is placed in an acrylic container 62 filled with water which can move with a precision of 0.1 mm by a computer-controlled actuator 63. In the experiment, it was assumed that a tumor 50 is displaced by 5 to 15 mm by respiration and its cycle continues for 4 to 6 seconds. The intensity of the $^{22}$Na$\beta^+$ radiation source 61 in this Example 1 was set at 1.2 MBp, which is equivalent to the intensity of FDG, which significantly affects a cancer with a diameter of 3 cm, 5 times higher than that on normal cells.

In the system of measurement, as shown in FIG. 6, a pair of gamma ray detectors 21,22 were disposed perpendicular to a moving direction (z direction) of the radiation source 61 with the water phantom in between. A scintillator of the gamma ray detectors 21,22 was a GSO(Gd$_2$SiO$_5$) single-crystal scintillator with a diameter of 2 inches. A collimator 23 prepared was a lead collimator 23 with a diameter of 3 cm, a lead collimator with a diameter of 1 cm or a focused collimator 23. A detection signal of annihilation gamma rays detected by the gamma ray detectors 21,22 was simultaneously counted to obtain counting rate, using simultaneous counting circuit.

Under the above conditions, the radiation source 61 (water phantom) displaced by 0.5 cm in z direction by the actuator 63 to calculate counting rate of an annihilation gamma ray at each measured position.

FIG. 7 shows the results of measurement using a lead collimator 23 with a diameter of 3 cm. When the radiation source 61 is at the center of a pair of gamma ray detectors 21,22 (z=0), the counting rate is highest. The counting rate becomes smaller as the radiation source 61 is displaced out of the center line between a pair of gamma ray detectors 21,22, and the counting rate is almost 0 when the displacement is 1.5 cm.

FIG. 8 shows the results of measurement using a lead collimator 23 with a diameter of 1 cm. As the lead collimator 23 with a diameter of 3 cm, the counting rate is highest at z=0, and the counting rate becomes smaller as the radiation source 61 is displaced.

According to the comparison between FIG. 7 and FIG. 8, it is obvious that the counting rate of an annihilation gamma ray is overall higher with a lead collimator 23 with the diameter of 3 cm than with a lead collimator 23 with the diameter of 1 cm. If the counting rate is overall low as shown in FIG. 8, errors with respect to a counting rate of 1 become larger. In this Example 1, since a difference in the counting rate of 1 causes an overall error of approx. 8%, the counting rate is preferably as high as possible. It was found that the lead collimator 23 with a diameter of 3 cm can detect displacement of a tumor 50 with a length of 5 mm or less. Using the lead collimator 23 with a diameter of 1 cm, the displacement of a tumor 50 with a length of 3 mm or less can be identified.

In this manner, in order to reduce the error of displacement of the tumor 50, the collimator 23 is appropriate in larger diameter, but smaller-diameter collimator 23 is appropriate to identify a smaller displacement. For example, if the tumor 50 is developed in the deep part inside the body or the volume of gamma rays from the radiation source 61 is small due to its small size, the collimator 23 is preferably designed in larger diameter to maintain high counting rate. Meanwhile, if annihilation gamma rays obtained from the radiation source 61 are sufficient, it is preferable to increase the sensitivity to displacement by preparing a collimator 23 in smaller diameter.

A collimator 23 can be a focused collimator 23. The focused collimator 23 is focused in any distance to improve position detection sensitivity as the counting rate is maintained. FIG. 9 shows the results of measurement using a focused collimator 23 which is focused on gamma ray detectors 21,22 in a distance of 15 cm. The focused collimator 23 is arranged so that the radiation source 61 is placed in a focal length. The radiation source 61 is displaced by 0.1 cm from a position of z=0 to 0.5 cm, and by 0.5 cm from a position of z=0.5 to 2.5 cm. As shown in comparison with FIG. 7, the counting rate is maintained high, and as it is displaced, the counting rate declines at a higher rate. Therefore, in order to detect the position of the tumor 50 more accurately, the focused collimator 23 is preferably employed.

Example 2

Next, standards for determining the threshold of counting rate of an annihilation gamma ray stored in the displacement threshold storage section 32 will be described in Example 2.

FIG. 10 shows the results of measurement when the radiation source is oscillation-displaced with an amplitude of 15 mm during a 5-second cycle, using a lead collimator 23 with a diameter of 3 cm. The relationship between the actual position of the radiation source and elapsed time is expressed by dotted line. The radiation source 61 is firstly placed at z=−15 mm and thereafter, it is displaced to a position of z=0 mm for approx. 1.4 seconds. After the radiation source 61 stays for about 2.2 seconds, it returns to the original position of z=−15 mm for approx. 1.4 seconds. The radiation source 61 repeatedly performed the oscillation displacement.

FIG. 10 shows the counting rate measured at an interval of 300 ms and its statistical error by polygonal line and error bar. The counting rate repeatedly increases and decreases substantially synchronously with radiation source displacement, and the displacement of the radiation source 61 can be specified according to the counting rate.

When the threshold of the counting rate is determined according to the results of FIG. 10, it is enough to find whether or not the counting rate is 130 cps or more in order to judge whether or not the radiation source 61 is at z=0. This is because that all positions of the radiation source in compliance with the counting rate of 130 cps or more range from z=−5 mm to 0 mm, the displacement of the radiation source 61 can be reduced to 5 mm or less, even in light of statistical error of counting.

Consequently, the threshold is determined by finding out a relationship between counting rate of an annihilation gamma ray and the displacement of the radiation source 61 prior to radiotherapy. Since a nuclide of an annihilation gamma ray declines as time elapses, the threshold can be determined by corresponding to an elapsed time. The threshold may be calculated at an appropriate time interval based on a function expression of elapsed time.

Example 3

Next, in Example 3, accuracy of tumor displacement measurement was examined by simulated computational calculation. FIG. 12 shows the results of calculation indicative of a relationship between count value of an annihilation gamma ray to the displacement of the tumor 50.

Computational calculation was simulated under the following conditions. As shown in FIG. 11, a human lung-shaped cylindrical lung phantom 65 with a diameter of 12 cm (density ($\rho$)=0.3 g/cm$^3$) is provided at the substantial center of a human-shaped regular-hexahedron human phantom 64 (density ($\rho$)=1.0 g/cm$^3$) with a side of 20 cm, in which a spherical tumor 50 with a diameter of 50 cm was placed. By defining the center of the tumor 50 as the initial position (z=0), count value to displacement in z direction was calculated.

The radiation source 61 from an annihilation gamma ray generated from the tumor 50 and phantoms 64,65 (normal cell) provides an intensity of 18.5 kBq/cc and 3.7 kBq/cc, respectively, as a substitute for F-fluorodeoxyglucose (FDG), and the annihilation gamma ray is emitted from the center of the tumor 50 in a radial and point-symmetry pattern.

The gamma ray detectors 21,22 are arranged in two pairs (4 units) so as to oppositely face with each other at an interval of about 50 cm perpendicular to z direction from a point of z=0. When a pair of annihilation gamma rays come in 2 gamma ray detectors 21,22, the probability of being simultaneously counted by 2 gamma ray detectors 21,22 (detection efficiency) was set at 0.68 according to measured values by actual equipment by GSO (Gd$_2$SiO$_5$) single-crystal scintillator with a diameter of 2 inches used in Example 1.

The count value was measured as the number of annihilation gamma rays detected in 300 ms by gamma ray detectors 21,22 by moving the tumor 50 on z axis. In this Example 3, the count value was measured when the tumor 50 was displaced along the z axis and stationary at each point.

FIG. 12 is a graph indicative of the results of measurement according to the above conditions. In the graph, a horizontal axis represents displacement of the center of the tumor 50 on the z axis, and a vertical axis represents mean count value of annihilation gamma rays detected in 300 ms by the gamma ray detectors 21,22. The error bar provided at the count value at each point denotes ±$\sigma$ with mean value as the center, based on standard deviation $\sigma$, a deviation from mean count value. Statistically, when a deviation from a mean value is set within ±$\sigma$, the probability of actual count value to be found within the ±$\sigma$ range is about 95%.

The upper limit of error bar at e.g. z=15 mm is about 155 counts/300 msec and the lower limit of error bar is about 140 counts/300 msec. When gamma rays are counted at z=15 mm, the count value ranges about 140 to 155 counts/300 msec with a probability of about 95%.

Likewise, the count value at z=20 mm ranges from about 120 to 135 counts/300 msec.

Next, accuracy of tumor displacement measurement is examined according to the above calculation results. It is known that the deviation of count value is expressed by Poisson distribution and the mean count value significantly exceeds 20, thereby providing an approximate value of a normal distribution. Statistically, a threshold is set at approx. 149 counts/300 msec as mean count value at a position of z=15 mm. Accordingly, when radiation irradiation means 10 irradiates the tumor with radiation after the count value measured exceeds the threshold, the radiation operation rate is about 50% and the probability of radiation error by 4 mm or more is approx. 1.22%. When a threshold is set at approx. 155 counts/300 msec as mean count value ($+\sigma$) or an upper limit of error bar, radiation operation rate is about 16% and the probability of radiation error by 4 mm or more is approx. 0.14%.

When the actual position of the tumor 50 is determined based on this Example 3, the following steps should be taken. Firstly, gamma ray detectors 21,22 are disposed perpendicular to z=15 mm in this Example 3, and a threshold for detecting the tumor 50 is set at a count value which is higher than mean count value at z=15 mm. When a count value measured by gamma ray detectors 21,22 is higher than the threshold, the tumor 50 is irradiated with radiation and when the value is lower than the threshold, radiation irradiation is stopped. As displacement specifying accuracy, the movement of the tumor 50 by 5 mm can be detected with a probability of 95% or more. The threshold is set in view of probability of allowable false irradiation and irradiation operation rate in the apparatus.

According to the above Examples 1 to 3, movement and position of the dynamic tumor can be specified, based on the counting rate of an annihilation gamma ray emitted from the radiation source 61. Also, on the basis of the threshold of the counting rate, whether or not the tumor 50 is found in the irradiation spot can be accurately judged.

Example 4

Next, Example 4, using time-of-flight method as gamma ray detecting means 20 in this embodiment, will be described. The time-of-flight method calculates a difference in arrival time of annihilation gamma rays which arrive at a pair of gamma ray detectors 21,22 and accordingly specifies the position of a radiation source in length direction between a pair of gamma ray detectors 21,22. FIG. 13 shows a schematic view of time-of-flight method.

General simultaneous counting is to count events of gamma rays simultaneously detected from a pair of gamma ray detectors 21,22. The gamma rays counted are emitted from the substantial center of the pair of gamma ray detectors 21,22. However, simultaneous counting is unable to find out the position of the radiation source 61 in length direction between the pair of gamma ray detectors 21,22. Due to this low sensitivity to the movement of the radiation source 61 in a direction of the gamma ray detectors, position detection accuracy is improved by placing another pair of gamma ray detectors 21,22 perpendicular thereto as well.

In fact, time-of-flight method improves accuracy in length direction between a pair of gamma ray detectors 21,22, which are conventionally required as two pairs, by setting any measuring region between a pair of gamma ray detectors 21,22 and detecting only an annihilation gamma ray emitted in the region.

For example, if a measuring region is provided on a detector 21 off the center between a pair of gamma ray detectors 21,22 in FIG. 13, a gamma ray emitted in the measuring region 51 reaches the detector 21 and thereafter a detector 22 with time difference. This Example 3 is able to simultaneously count gamma rays in view of the time difference and judge whether or not radiation source 61 is in the measuring region 51 based on the counting rate.

According to the above Example 4, the entire apparatus can be designed in simpler manner and an annihilation gamma ray emitted from a radiopharmaceutical which accumulates in the tumor 50 can be efficiently measured.

Example 5

Next, Example 5, in which the movement of a tumor 50 which is three-dimensionally displaced can be accurately detected and spatial accuracy can be improved by providing a plurality of measuring regions near the border between the tumor 50 and a normal cell, will be described.

FIG. 5 shows a positional relationship between a tumor 50 and a measuring region when the position of a tumor 50 is detected by 4 pairs of gamma ray detectors 21,22. There are two methods for providing a measuring region 51 near the border: a method for irradiating the tumor 50 with radiation when all counting rates in a measuring region 51 are the threshold or more and disabling radiation irradiation means 10 when any one of the counting rates is the threshold or less (see FIG. 5(A)), and another method for irradiating the tumor 50 with radiation when counting rates in all measuring regions are the threshold or less and disabling the radiation irradiation means 10 when any one of the counting rates is the threshold or more (see FIG. 5(B)). The corresponding examples are described.

Firstly, a method for irradiating the tumor 50 with radiation when counting rates in all measuring regions 51 are the threshold or more is described. In this method, a measuring region 51 and a radiation irradiation spot are determined for a tumor 50 whose position and movement are detected in advance. The measuring region 51 is provided at a tumor boundary part 52. A tumor position judging section 44 judges that the tumor 50 exists in the radiation irradiation spot when the counting rates of annihilation gamma rays are the threshold or more in all measuring regions, and conversely the tumor 50 is displaced out of the radiation irradiation spot when the counting rates of annihilation gamma rays are the threshold or less in any one of the measuring regions 51. If the tumor 50 is found in the radiation irradiation spot, the radiation irradiation means 20 irradiates the tumor 50 in the radiation irradiation spot with radiation to annihilate the tumor 50.

Next, another method for enabling radiation irradiation means 20 when counting rates in all measuring regions 51 are the threshold or less is described. In this method, the position and movement of the tumor 50 are detected to determine a measuring region 51 and an irradiation spot. The measuring region 51 is set at a boundary part of a stationary displaced tumor 53 of the tumor 50. A tumor position judging section 44 judges that the tumor 50 exists in the radiation irradiation spot when the counting rates of annihilation gamma rays are the threshold or less in all measuring regions 51, and the tumor 50 is displaced out of the radiation irradiation spot when the counting rates of annihilation gamma rays are the threshold or more in any one of the measuring regions 51. When the tumor 50 is found in the radiation irradiation spot, the tumor 50 in the radiation irradiation spot is irradiated with radiation to annihilate the tumor 50.

In this way, the movement of the tumor 50 which is three-dimensionally displaced can be accurately detected and radiation irradiation on non-tumor cells can be significantly reduced.

A dynamic tumor radiation treatment apparatus 1 and a dynamic tumor radiation treatment program according to the present invention are not limited in the above Examples, but may be altered accordingly.

For example, the gamma ray detecting means 20 and the radiation treatment program in Example 4 may correspond to time-of-flight method. Accordingly, since annihilation gamma rays only detected from the tumor 50 can be measured, resulting in improvement in signal/noise rate and determination accuracy of tumor region.

The counting rate computing section 41 of the computing means 20 may be provided with the gamma ray detecting means 20.

BRIEF DESCRIPTION OF THE DRAWINGS

The above and other objects in this invention will be seen by reference to the description taken in connection with the drawings, in which.

EXPLANATION OF LETTERS OR NUMERALS

Figure 1:
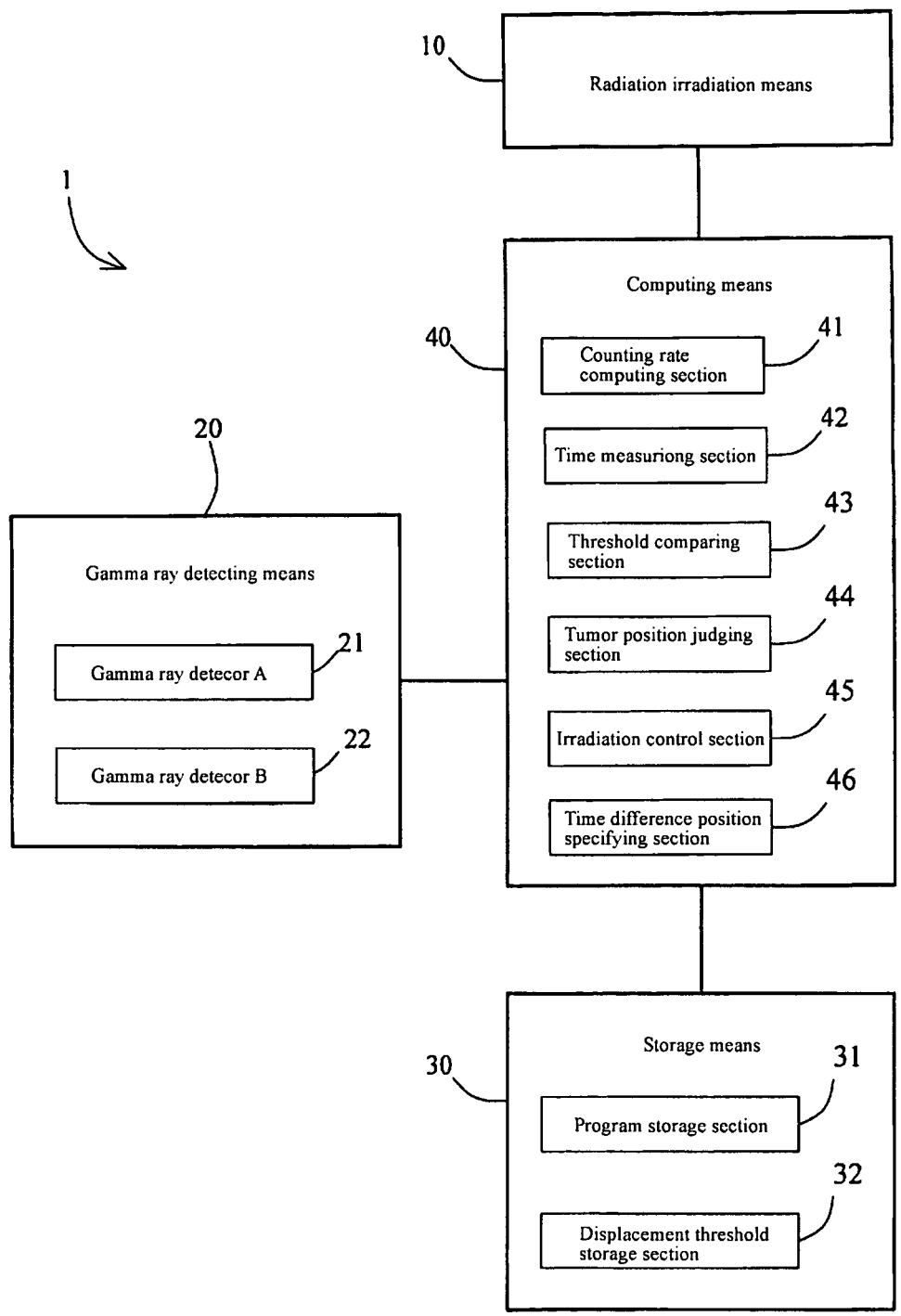
FIG. 1 is a block diagram indicative of overall structure of a first embodiment of a dynamic tumor radiation treatment apparatus according to the present invention.
Figure 2:
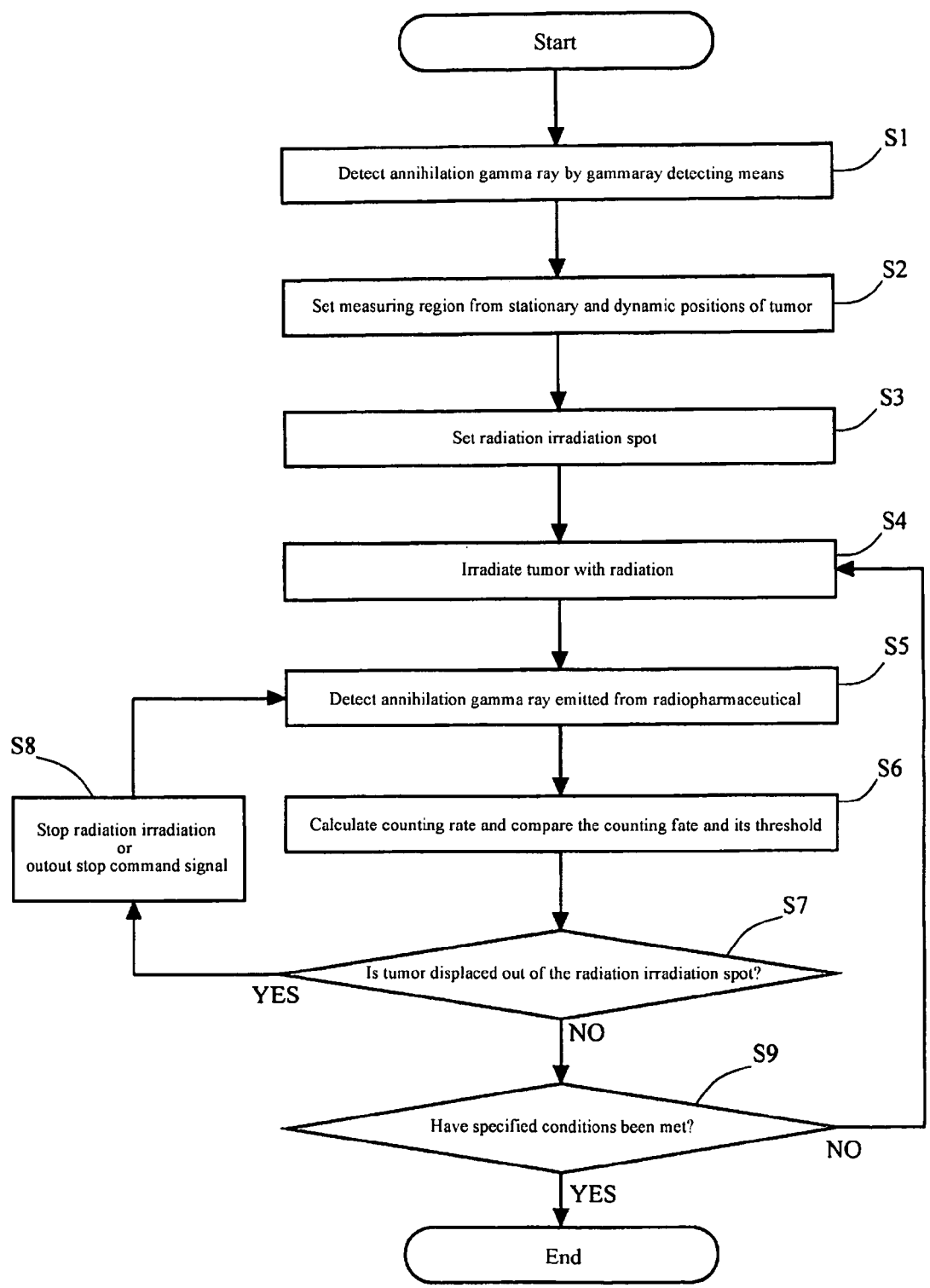
FIG. 2 is a flow chart indicative of the operation of a dynamic tumor radiation treatment apparatus executed by a dynamic tumor radiation treatment program in this first embodiment.
Figure 3:
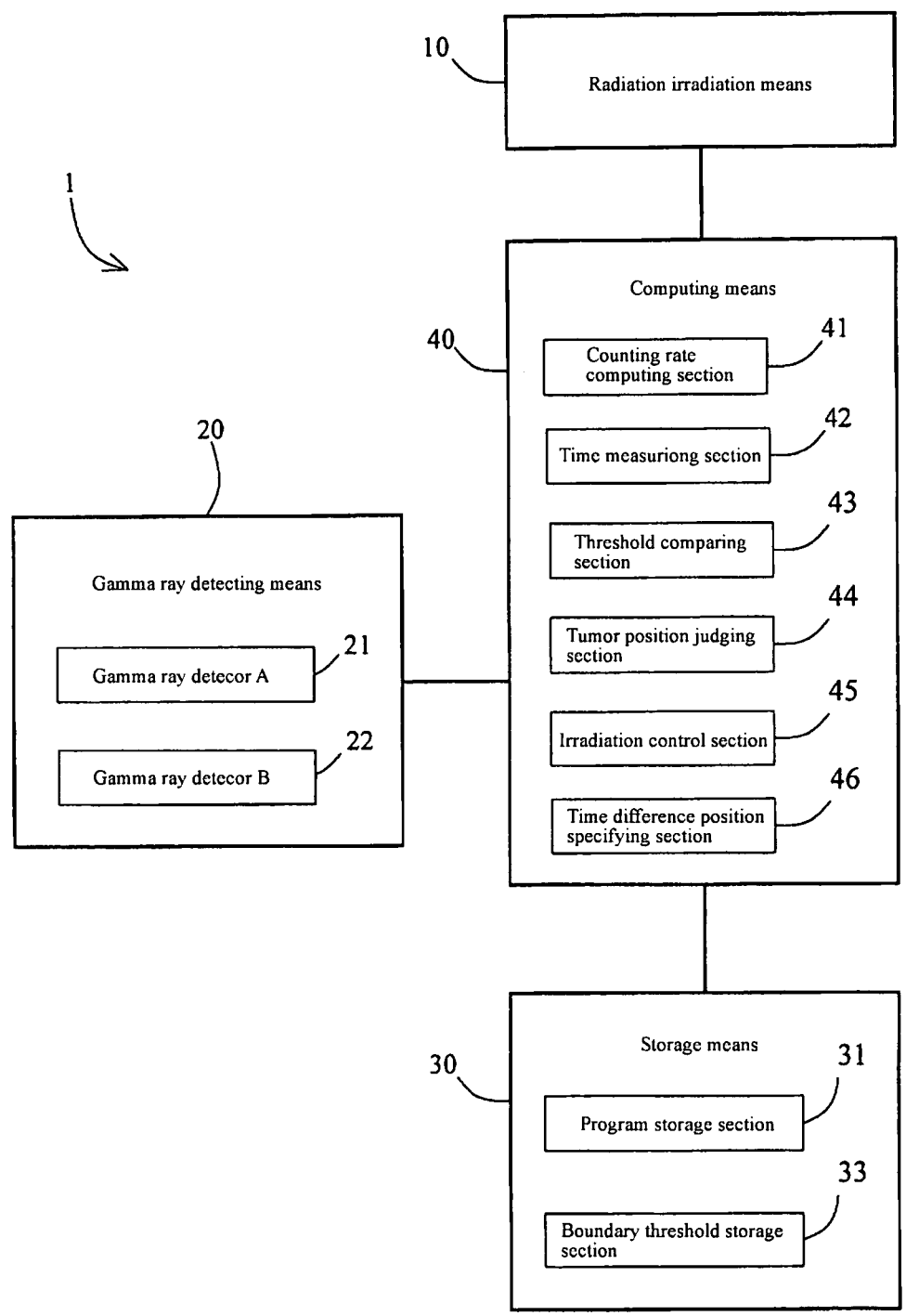
FIG. 3 is a block diagram indicative of overall structure of this second embodiment.
Figure 4:
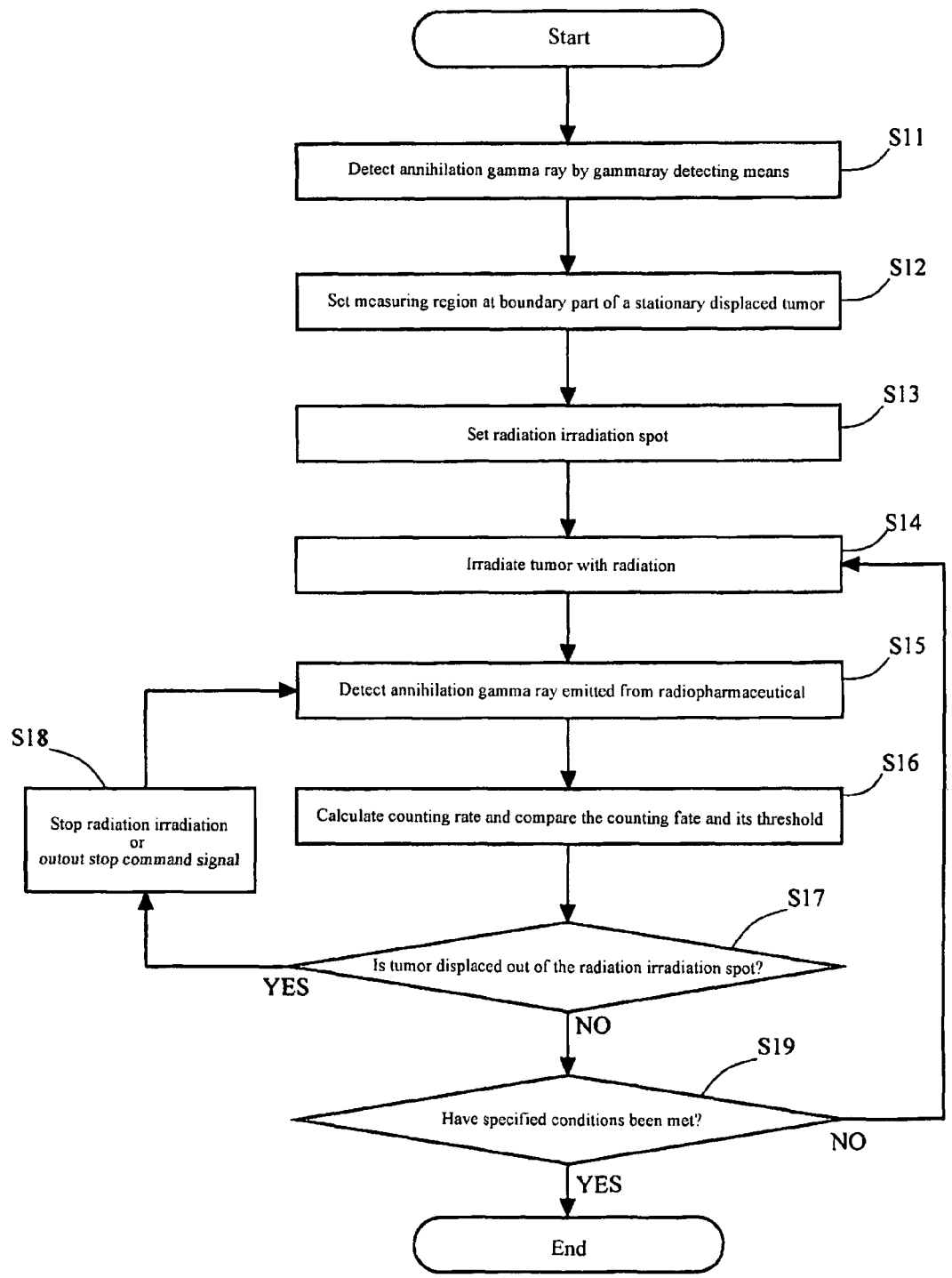
FIG. 4 is a flow chart indicative of the operation of a dynamic tumor radiation treatment apparatus executed by a dynamic tumor radiation treatment program in this second embodiment.
Figure 5:
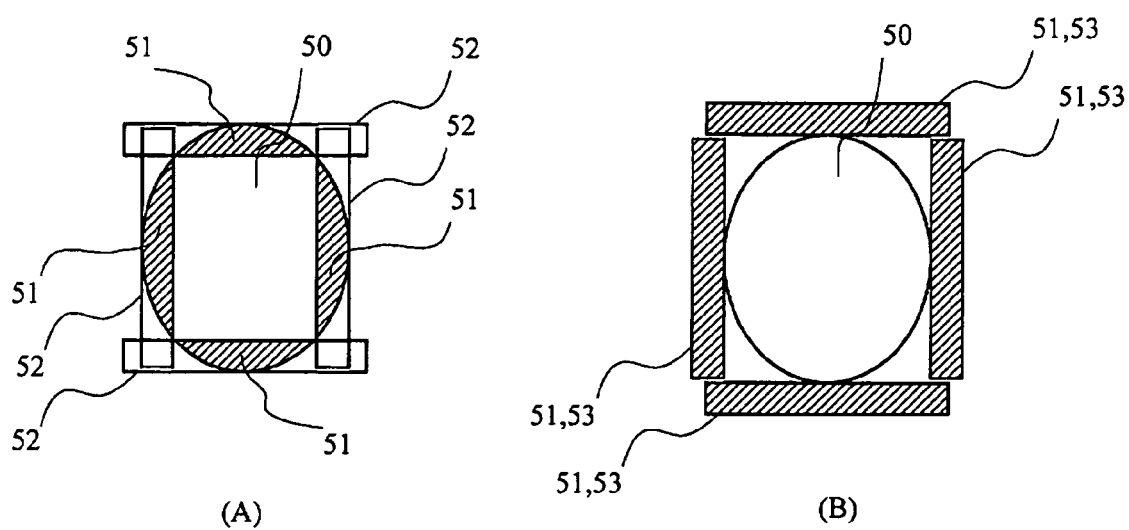
FIG. 5 is a schematic view indicative of a positional relationship between tumor and measuring region in this second embodiment.
Figure 6:
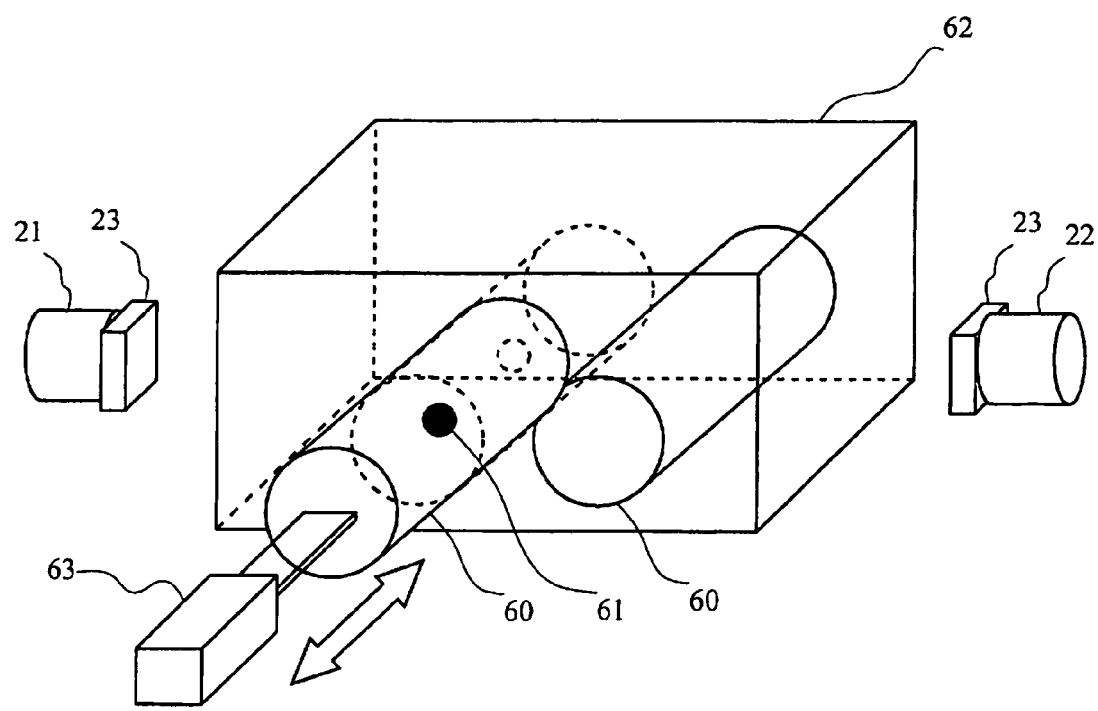
FIG. 6 is a schematic view indicative of a water phantom for a human lung used in the experiment.
Figure 7:
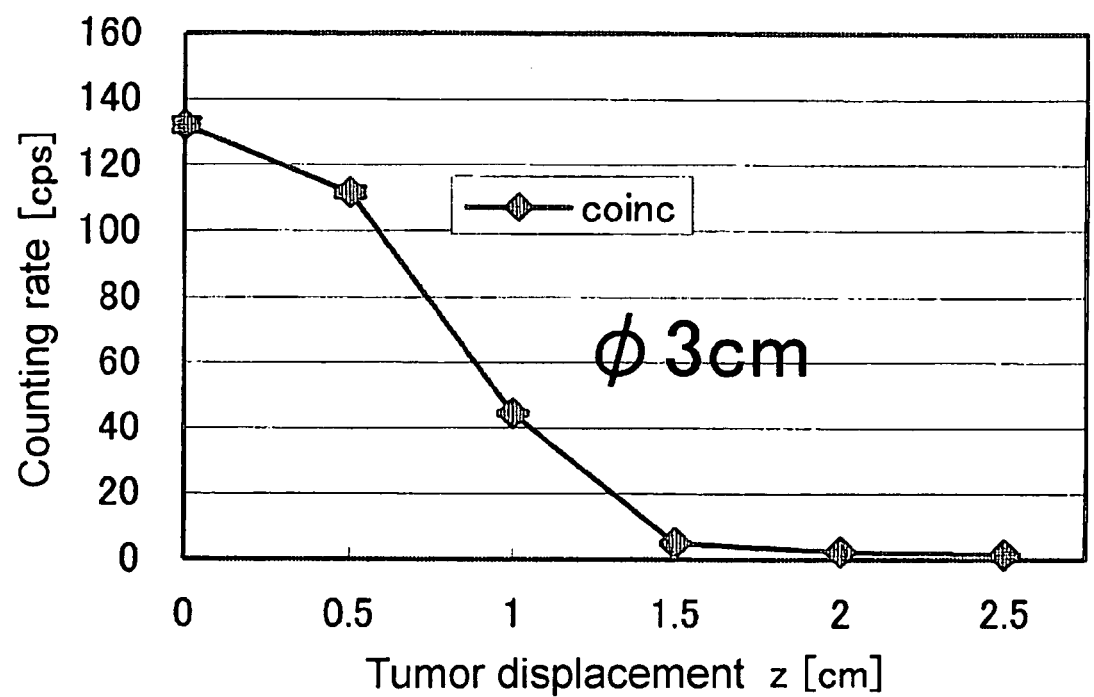
FIG. 7 a graph indicative of the results of measurement using a lead collimator with a diameter of 3 cm in this Example 1.
Figure 8:
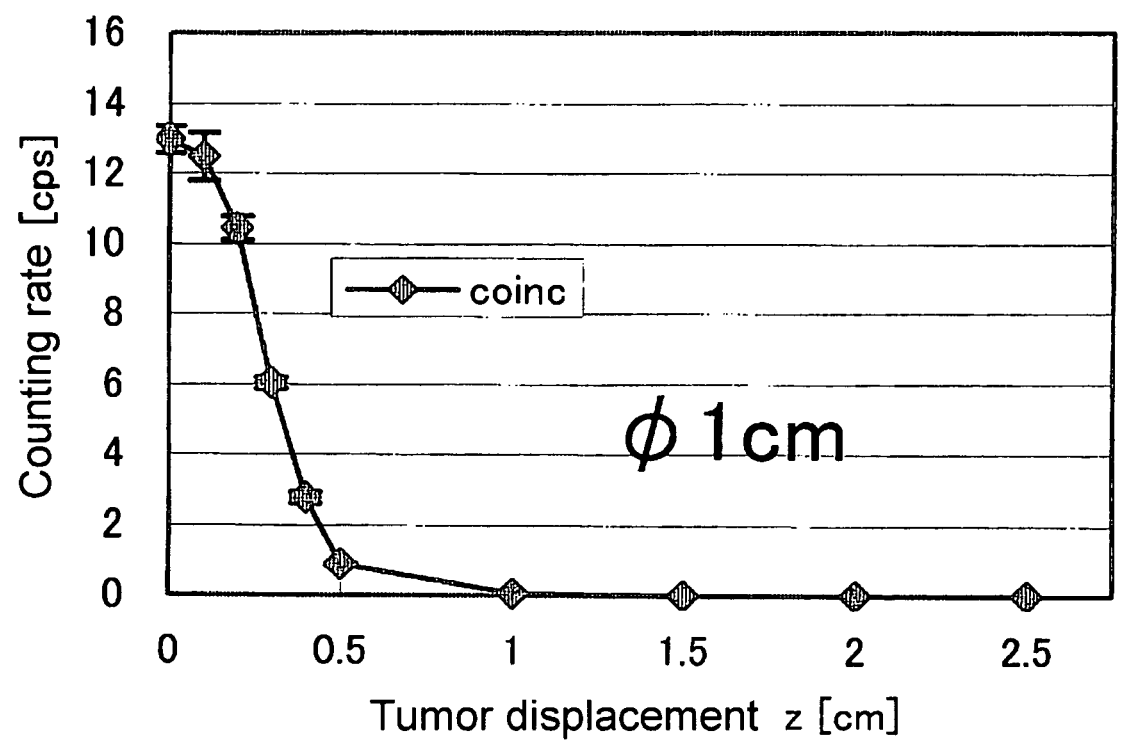
FIG. 8 a graph indicative of the results of measurement using a lead collimator with a diameter of 1 cm in this Example 1.
Figure 9:
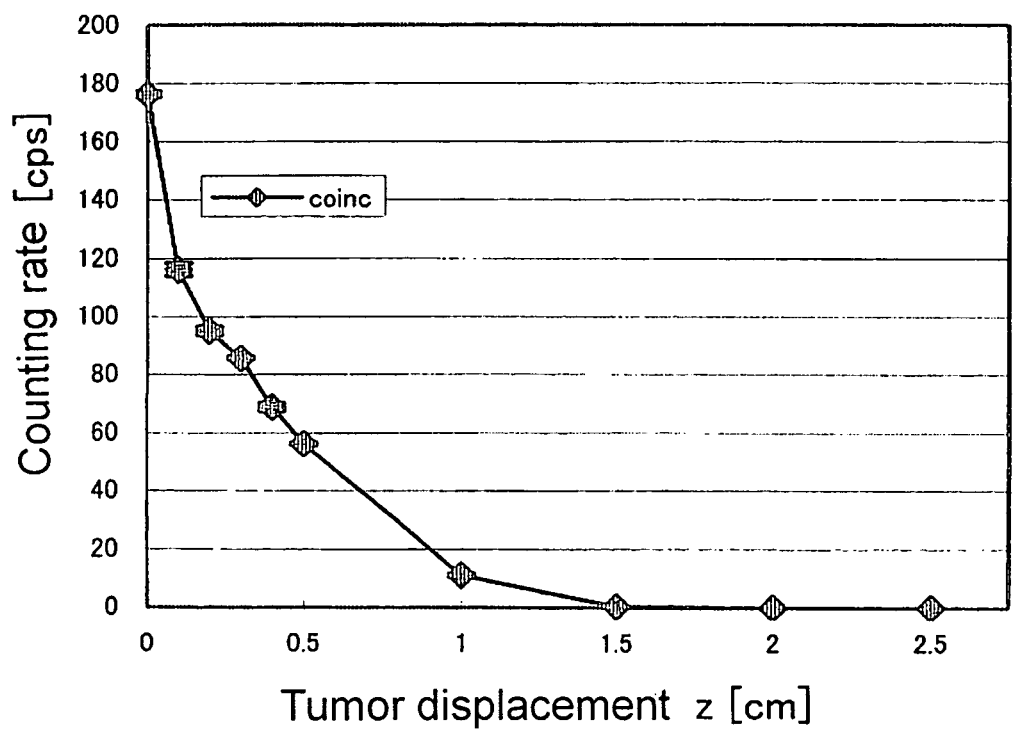
FIG. 9 a graph indicative of the results of measurement using a focused collimator in this Example 1.
Figure 10:
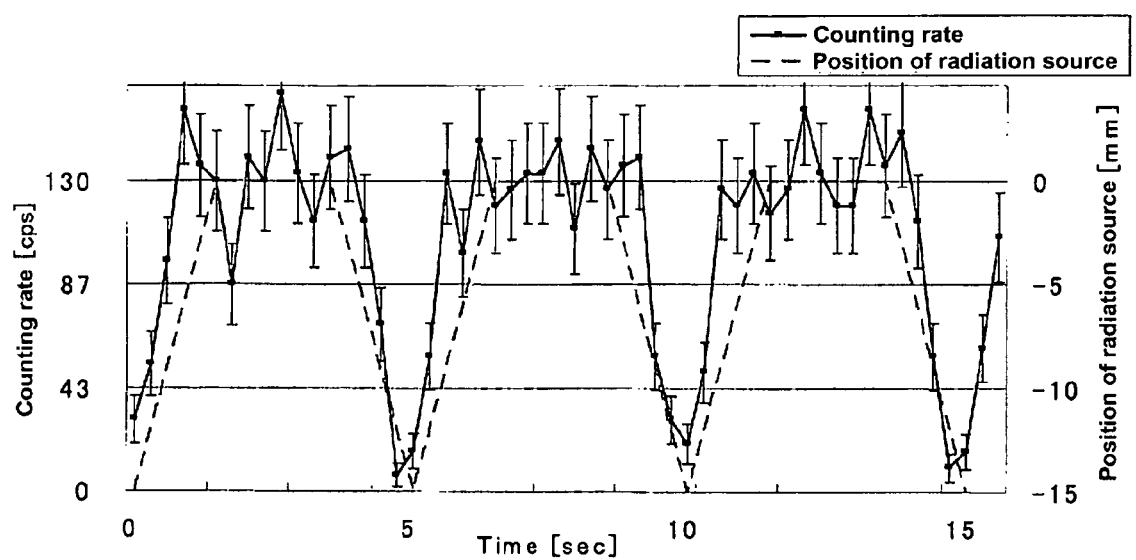
FIG. 10 a graph indicative of the results of measurement when the radiation source is oscillation-displaced with an amplitude of 15 mm during 5-second cycle, using a lead collimator with a diameter of 3 cm in this Example 2.
Figure 11:
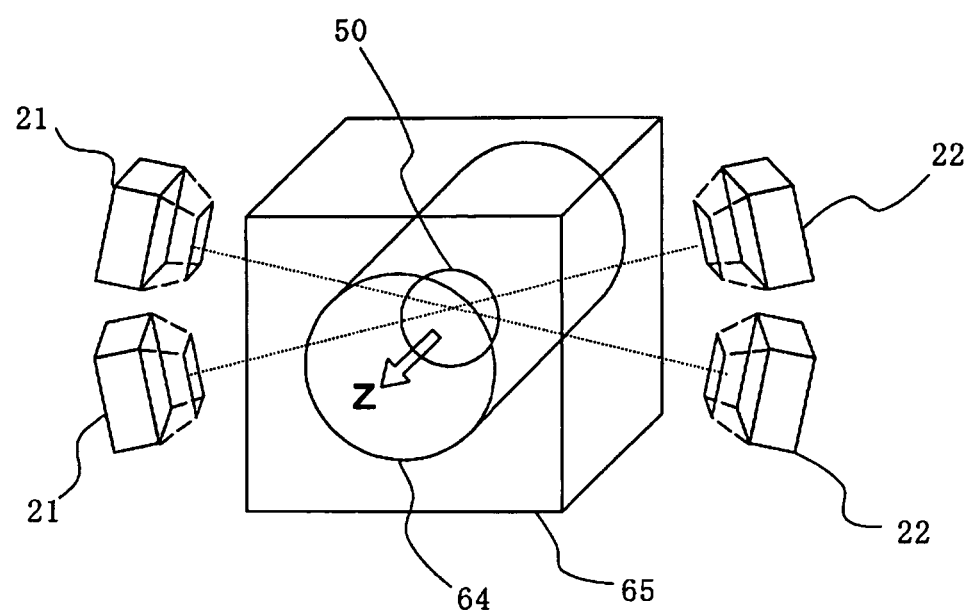
FIG. 11 is a perspective view indicative of a positional relationship between tumor and gamma ray detector in this Example 3.
Figure 12:
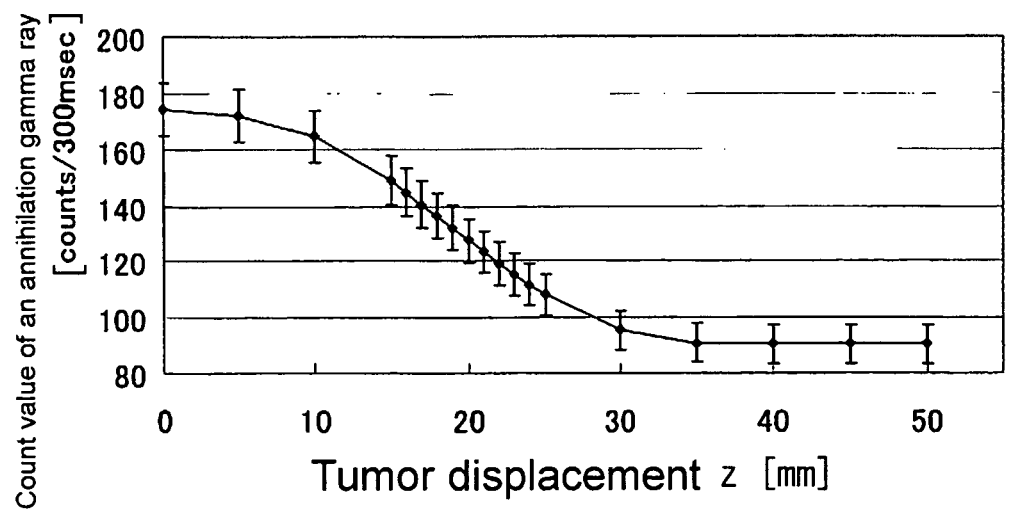
FIG. 12 is a graph indicative of the results of calculation indicative of a relationship between annihilation gamma ray count value and tumor displacement in this Example 3.
Figure 13:
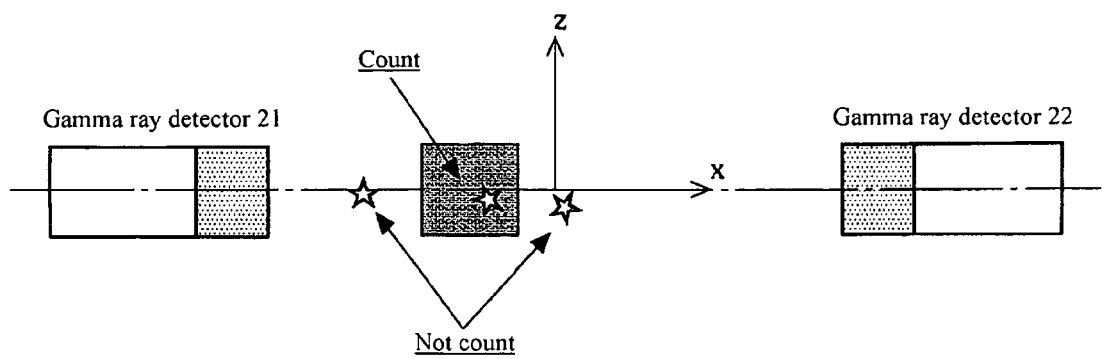
FIG. 13 is a schematic view of time-of-flight method in Example 4.

1 Dynamic tumor radiation treatment apparatus
10 Radiation irradiation means
20 Gamma ray detecting means
30 Storage means
40 Computing means
50 Tumor
60 Water phantom
21 Gamma ray detector
22 Gamma ray detector
23 Collimator
31 Program storage section
32 Displacement threshold storage section
33 Boundary threshold storage section
41 Counting rate computing section
42 Time measuring section
43 Threshold comparing section
44 Tumor position judging section
45 Irradiation control section
46 Time difference position specifying section
51 Measuring region
52 Tumor boundary part
53 Boundary part of a stationary displaced tumor
61 Radiation source
62 Acrylic container
63 Actuator
64 Human phantom
65 Human lung phantom

The invention claimed is:

1. A dynamic tumor radiation treatment apparatus, comprising:
   gamma ray detecting means for detecting an annihilation gamma ray emitted from a radiopharmaceutical that accumulates in a tumor by dosing in vivo;
   displacement threshold storage means for storing a threshold of counting rate according to a relationship between said counting rate of the annihilation gamma ray and a displacement of a radiation source;
   gamma ray counting rate computing means for computing the counting rate according to a detection signal of the annihilation gamma ray detected by said gamma ray detecting means;
   threshold comparing means for comparing the counting rate of annihilation gamma rays acquired from said gamma ray counting rate computing means with the threshold of the counting rate acquired from said displacement threshold storage means;
   tumor position judging means for judging whether or not the tumor is displaced out of a radiation irradiation spot according to results by said threshold comparing means; and
   irradiation control means for making a control to stop radiation irradiation by a therapeutic radiation irradiation means when said tumor position judging means judges that the tumor is displaced out of the radiation irradiation spot or for outputting a stop command signal.

2. The dynamic tumor radiation treatment apparatus as set forth in claim 1, wherein:
   said gamma ray detecting means detects the annihilation gamma ray by a pair of gamma ray detectors oppositely disposed with a tumor in between and said gamma ray counting rate computing means computes a counting rate by simultaneously counting annihilation gamma rays.

3. A dynamic tumor radiation treatment apparatus, comprising:
   gamma ray detecting means for detecting an annihilation gamma ray emitted from a radiopharmaceutical that accumulates in a tumor by dosing in vivo by setting a plurality of measuring regions at a tumor boundary part or a boundary part of a stationary displaced tumor;

boundary threshold storage means for storing the threshold of counting rate according to a relationship between said counting rate of the annihilation gamma ray and a displacement of a radiation source;

gamma ray counting rate computing means for computing the counting rate according to a detection signal of an annihilation gamma ray detected by said gamma ray detecting means;

threshold comparing means for comparing the counting rate of annihilation gamma rays acquired from said gamma ray counting rate computing means with the threshold of the counting rate acquired from said boundary threshold storage means;

tumor position judging means for judging whether or not the tumor is displaced out of a radiation irradiation spot according to results by said threshold comparing means; and irradiation control means for making a control to stop radiation irradiation by a therapeutic radiation irradiation means when said tumor position judging means judges that the tumor is displaced out of the radiation irradiation spot or for outputting a stop command signal.

4. The dynamic tumor radiation treatment apparatus as set forth in claim 3, wherein said gamma ray detecting means computes counting rate of an annihilation gamma ray with a pair of gamma ray detectors oppositely disposed in each measuring region so that said gamma ray counting rate computing means simultaneously computes annihilation gamma rays detected by the pair of gamma ray detectors.

5. The dynamic tumor radiation treatment apparatus as set forth in one of claims 1 or 3, wherein the threshold comparing means acquires a threshold at a point of time according to counting rate of an annihilation gamma ray which declines as time elapses.

6. The dynamic tumor radiation treatment apparatus as set forth in one of claims 2 or 4, wherein said gamma ray detecting means calculates counting rate by oppositely disposing another pair of gamma ray detectors oppositely disposed in crossing direction to said pair of gamma ray detectors oppositely disposed, so that said gamma ray counting rate computing means simultaneously counts annihilation gamma rays.

7. The dynamic tumor radiation treatment apparatus as set forth in one of claims 2 or 4, comprising time difference position specifying means for specifying a position of a radiation source in length direction between said pair of gamma ray detectors by calculating a difference in arrival time of an annihilation gamma ray which arrives at said pair of gamma ray detectors.

8. A dynamic tumor radiation treatment program for causing a computer to function by the program, wherein the program comprises:

detecting an annihilation gamma ray emitted from a radiopharmaceutical that accumulates in a tumor by dosing in vivo with a gamma ray detecting means;

storing threshold of counting rate according to a relationship between said counting rate of the annihilation gamma ray and a displacement of a radiation source with a displacement threshold storage means;

computing a counting rate according to a detection signal of an annihilation gamma ray detected by said gamma ray detecting means with a gamma ray counting rate computing means;

comparing the counting rate of annihilation gamma rays acquired from said gamma ray counting rate computing means with the threshold of the counting rate acquired from said displacement threshold storage means with a threshold comparing means;

judging whether or not the tumor is displaced out of a radiation irradiation spot according to results by said threshold comparing means with a tumor position judging means; and making a control to stop radiation irradiation by a therapeutic radiation irradiation means when said tumor position judging means judges that the tumor is displaced out of the radiation irradiation spot or for outputting a stop command signal.

9. A dynamic tumor radiation treatment program for causing a computer to function by the program, wherein the program comprises:

detecting an annihilation gamma ray emitted from a radiopharmaceutical that accumulates in a tumor by dosing in vivo by setting a plurality of measuring regions at a tumor boundary part or a boundary part of a stationary displaced tumor with a gamma ray detecting means;

storing a threshold of counting rate according to a relationship between said counting rate of the annihilation gamma ray and the displacement of a radiation source in a measuring region with a boundary threshold storage means;

computing the counting rate according to a detection signal of an annihilation gamma ray detected by said gamma ray detecting means with a gamma ray counting rate computing means;

comparing with a threshold comparing means the counting rate of annihilation gamma rays acquired from said gamma ray counting rate computing means with the threshold of the counting rate acquired from said displacement threshold storage means;

judging whether or not the tumor is displaced out of a radiation irradiation spot according to results by said threshold comparing means with a tumor position judging means; and controlling with a irradiation control means to stop radiation irradiation by a therapeutic radiation irradiation means when said tumor position judging means judges that the tumor is displaced out of the radiation irradiation spot or for outputting a stop command signal.

* * * * *